United States Patent [19]

Misselhorn et al.

[11] Patent Number: 4,715,932

[45] Date of Patent: Dec. 29, 1987

[54] METHOD TO SEPARATE POLAR ORGANIC COMPOUNDS, IN PARTICULAR ALIPHATIC ALCOHOLS, FROM FERMENTATION FLUIDS

[76] Inventors: Klaus Misselhorn, Ascheberger Weg 41, 1000 Berlin 27; Uwe Tegtmeier, Triftstrasse 46, 1000 Berlin 65, both of Fed. Rep. of Germany

[21] Appl. No.: 361,069

[22] Filed: Mar. 23, 1982

[30] Foreign Application Priority Data

Mar. 30, 1981 [DE] Fed. Rep. of Germany ....... 3112603

[51] Int. Cl.$^4$ ........................ B01D 3/34; C07C 29/86
[52] U.S. Cl. ........................ 203/43; 203/19; 203/DIG. 13; 435/161; 568/916; 568/918
[58] Field of Search ................ 568/918–920, 568/916, 913; 562/513, 607–609; 435/161; 44/53; 203/14, 15, 16, 18, 19, DIG. 13, 43–46

[56] References Cited

U.S. PATENT DOCUMENTS

| | | | |
|---|---|---|---|
| 2,591,671 | 4/1952 | Catterall | 203/18 |
| 2,614,971 | 10/1952 | Burton | 203/18 |
| 2,644,006 | 6/1953 | vander Waals | 568/918 |
| 2,801,957 | 8/1957 | Ray | 203/45 |
| 2,953,502 | 9/1960 | Binning et al. | 203/14 |
| 3,052,731 | 9/1962 | Murphy | 568/918 |
| 4,306,884 | 12/1981 | Roth | 568/918 |
| 4,346,241 | 8/1982 | Feldman | 203/22 |
| 4,399,000 | 8/1983 | Tedder | 203/DIG. 13 |
| 4,400,241 | 8/1983 | Braithwaite et al. | 203/DIG. 13 |

*Primary Examiner*—Wilbur Bascomb
*Attorney, Agent, or Firm*—Wenderoth, Lind & Ponack

[57] ABSTRACT

This invention relates to a method for separating organic compounds, particularly lower aliphatic alcohols from fermentation fluids. This is accomplished by the use of a two-step extraction process whereby said lower aliphatic alcohols are selectively extracted from said fermentation fluids by a first solvent. The fermentation fluids from which the lower aliphatic alcohols have been extracted contain some of this first solvent. Therefore, a second solvent, which substantially differs from the first solvent in polarity is employed to extract the residual amounts of first solvent from said fermentation fluids. Then, the fermentation fluids, thus purified, can be returned to the fermentation process without the danger of toxic influences on the fermentation by the presence of said first solvent.

12 Claims, 6 Drawing Figures

METHOD TO SEPARATE POLAR ORGANIC COMPOUNDS, IN PARTICULAR ALIPHATIC ALCOHOLS, FROM FERMENTATION FLUIDS

BACKGROUND AND PRIOR ART

The invention concerns a method for the separation of polar organic compounds, preferably lower aliphatic alcohols, from an aqueous solution. In accordance with this invention, it is done with a liquid/liquid extraction. The aqueous solution is a fermentation liquid, which contains the dissolved portions of the polar organic compounds. Hereinafter, this fermentation liquid is referred to as "mash".

Production of ethanol, for example, as a liquid, transportable energy source has recently become more important for various reasons. Because of the shortage of energy resources in the world, particularly oil, ethanol has gained increased recognition as one of the alternative energy sources, that is, as basic industrial raw material as well as fuel. Several countries have already committed their energy policy to include the utilization of ethanol.

The use of local agricultural raw materials has the economic advantage of saving foreign currency for those countries which do not control any fossilized energy resources. Another positive aspect is the contribution of plant carbon to the carbon cycle, that is the use of solar energy.

The industrial technical production of ethanol requires improved, more economical and, with respect to the energy balance, more promising production processes than those which now can be considered the level of technology, which includes the periodically operating (batch) method. This also includes the necessity to operate fermentation as well as recovery of the fermentation alcohol on a continuous basis. The latter is already in use with batch and/or semi-continuous fermentation.

It is known that during the biochemical conversion from sugar to ethanol and $CO_2$ with the aid of yeast, ethanol production can be increased by limiting the ethanol concentration in the fermentation fluid.

We are familiar with various methods, which deal iwth the removal of ethanol from the mash during fermentation, either through binary or through ternary vacuum azeotropic distillation at fermentation temperature. All of these methods, however, are not economical for large-scale production because the creation of a sufficiently high vacuum requires a lot of energy due to the $CO_2$, which forms and is dissolved in the mash, and because the necessary equipment has to have large dimensions.

With ternary azeotropic distillation, it is also important to consider the fact that a suitable azeotropic developer is hard to find, which can be used sensibly with the existing pressure conditions and which also does not unfavorably influence yeast activity.

If ethanol is produced on a large scale, it is accompanied by a high accumulation of an ethanol-free watery solution, which in the following is called "distiller's wash." The amount of distiller's wash, which flows off in the end, depends on the sugar content of the substratum solution, added to the fermention, and on the amount of dry substance in the fermentation solution. The latter strongly influences the amount of energy necessary to boil down the distiller's wash. It also points out a possible way to sensibly use this waste product. The amount of dry substance in the mash can be increased by partially maintaining the watery fermentation fluid cycle.

OBJECTS AND BRIEF SUMMARY OF THE INVENTION

It is the task of the invention at hand to provide a method of the above-mentioned kind, which allows the continuous separation of the product, which forms in the mash through fermention, preferably ethanol or other alcohol products, and which makes it possible to have a continuous fermentation process with accompanying limitation of the ethanol content and increase of the dry content of the aqueous phase, by allowing the fermentation solution with lowered ethanol content to be returned without damage to the yeast.

This task is solved in the invention by:

(a) extracting at least part of said fermentation fluid from a fermentation process with a first solvent (SI) which is a selective extractant for said polar organic compounds to form an extract phase (EI) and a first raffinate phase (RI);

(b) separating said first extract phase (EI) from said first raffinate (RI);

(c) recovering said polar organic compounds from said first extract phase (EI);

(d) extracting said first raffinate (RI), which contains some solvent (SI), with a second solvent (SII) which is a selective solvent for first solvent (SI) and which has a different polarity than solvent (SI) to form a second extract phase (EII) and a second raffinate (RII); and, (e) separating said second extract phase (EII) from said second raffinate (RII), whereby said phase RII is substantially free from said solvent (SI), solvent (SII) and said polar organic compounds.

The two necessary extraction steps are preferably done in a pulsating perforated-bottom extraction plant. In accordance with the invention, aqueous solutions with a certain amount of particulate solids and dirt are to be filtered through the extractor. Perforated bottom extraction plants have the advantage of high capacity with low back mixture, a low height for a theoretical separating floor—and thus a low plant height—and a defined concentration profile. This simplifies the contruction of such a plant under the given conditions.

It is of advantage to run the recovery process (in particular the extraction) parallel to a continously operating fermentation. However, it is possible, with use of raffinate II as processing water and with existing buffer capacity, to combine a periodic fermentation process with the extraction measures.

BRIEF DESCRIPTION OF THE DRAWINGS

In the following, the inventive method will be described with reference to the attached figures, whereby.

DETAILED DESCRIPTION

Figure 1:
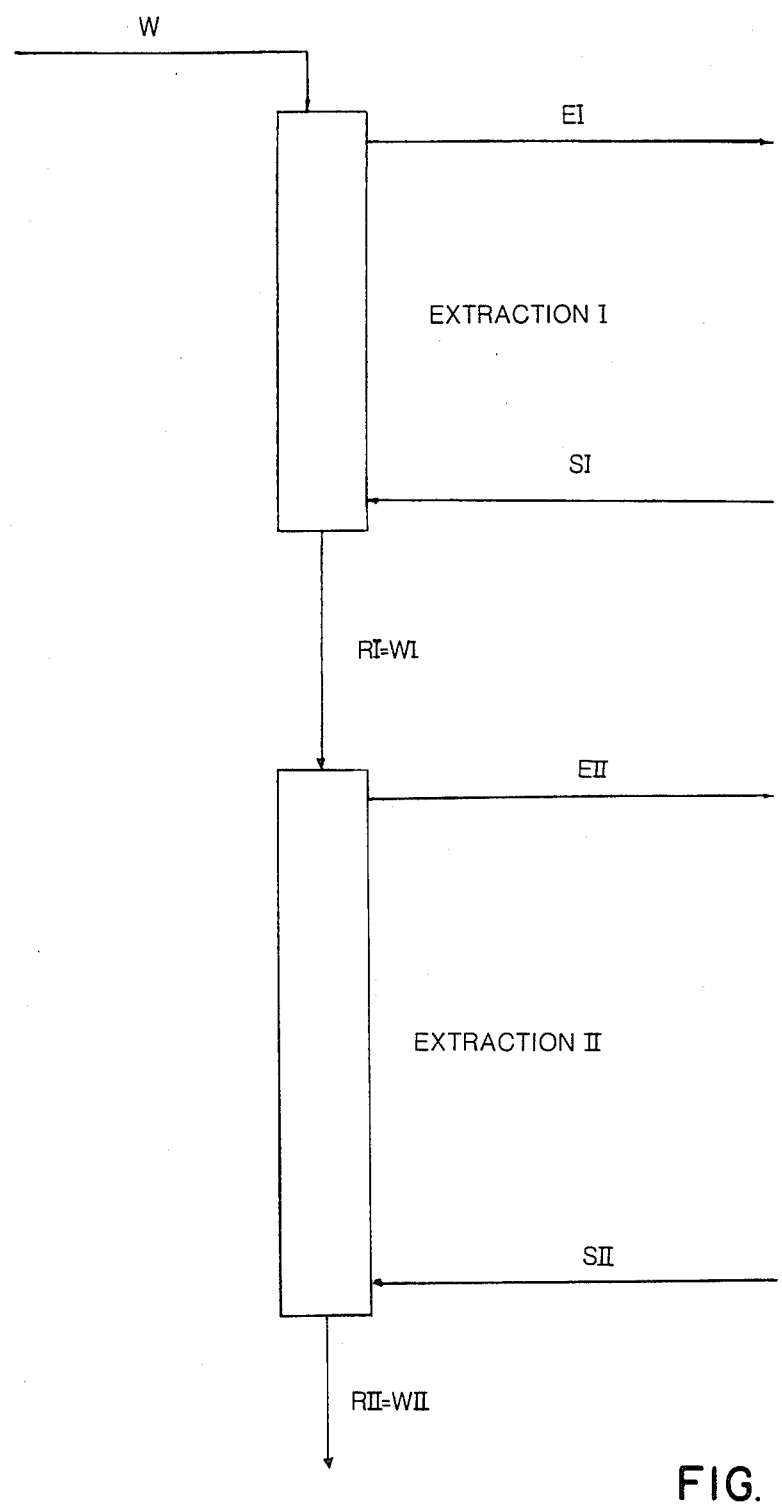
FIG. 1 is a basic flow diagram for the method in accordance with the invention.

For the first extraction step (FIG. 1), it is necessary to use a solvent (SI) in an aqueous solution (W), which is sufficiently selective with respect to ethanol. In general, this requires a considerable increase in the solvent I (SI) portion in the raffinate I (RI), which flows off. For that version of the method, shown in FIG. 2, it is desirable that in the subsequent recovery of extract phase I (EI) through distillation, no ternary azeotrope is formed between solvent I (SI), ethanol and the residual water content. This would make a 100% recovery of extraction solvent I (SI) very difficult.

Because of the two reasons mentioned (selectivity, formation of azeotrope), the argument is for use of a higher alcohol as extraction solvent I. One example for such a solvent is n-hexanol.

Figure 3:
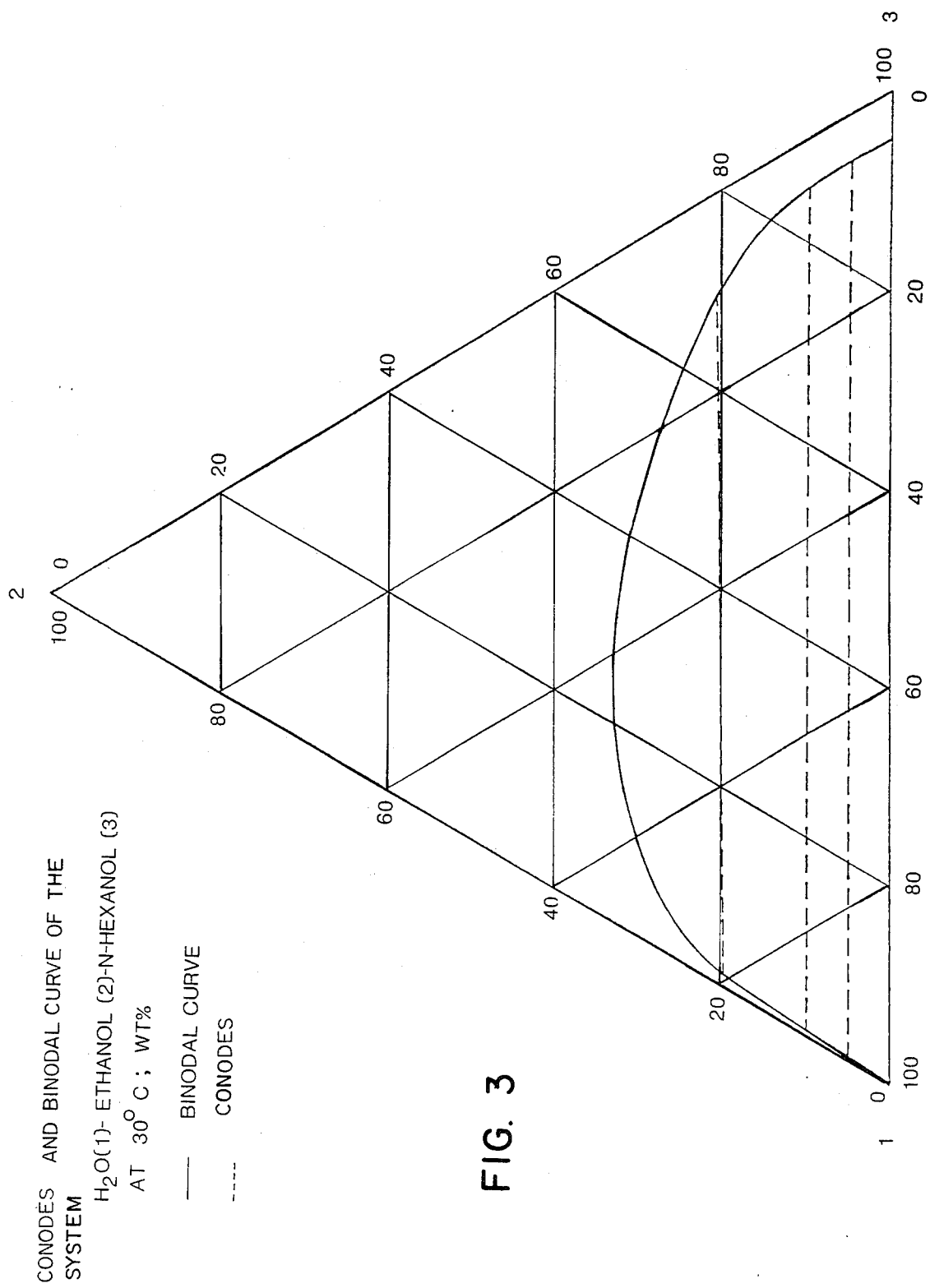

FIG. 3 is an illustration of the fluid/fluid equilibrium behavior of the $H_2O(1)$-ethanol(2)-n-hexanol(3) system. The position of the binodal curve serves to describe the mutual solubility behavior of coexisting phases, while the inclination of the conodes is a measure of the corresponding selectivities, which depend on the concentration. The raffinate I, which flows off after the first extraction, has an approximate n-hexanol content of max. 1% by weight. In the course of the process, this value increases to about 2% by weight due to mash components, which change the solution and act to disperse it. Because of this composition of substances, it is not possible to return outflowing refined phase I to the fermentation process as it will immediately cut down the activity of the yeast, and the resulting loss of solvent will make the whole process uneconomical.

By means of a second, connected extraction system II (FIG. 2), the solvent I (SI) of raffinate I (RI) is removed almost completely and can be separated and recovered from solvent II (SII), used in extraction II, through distillation.

As extraction solvent II (SII), solvent of low polarity has to be chosen in order to strongly increase the selectivity of this solvent to solvent I (SI) and in order to keep the solubility of solvent II as low as possible in raffinate II (RII) which flows off at the end.

Figure 4:
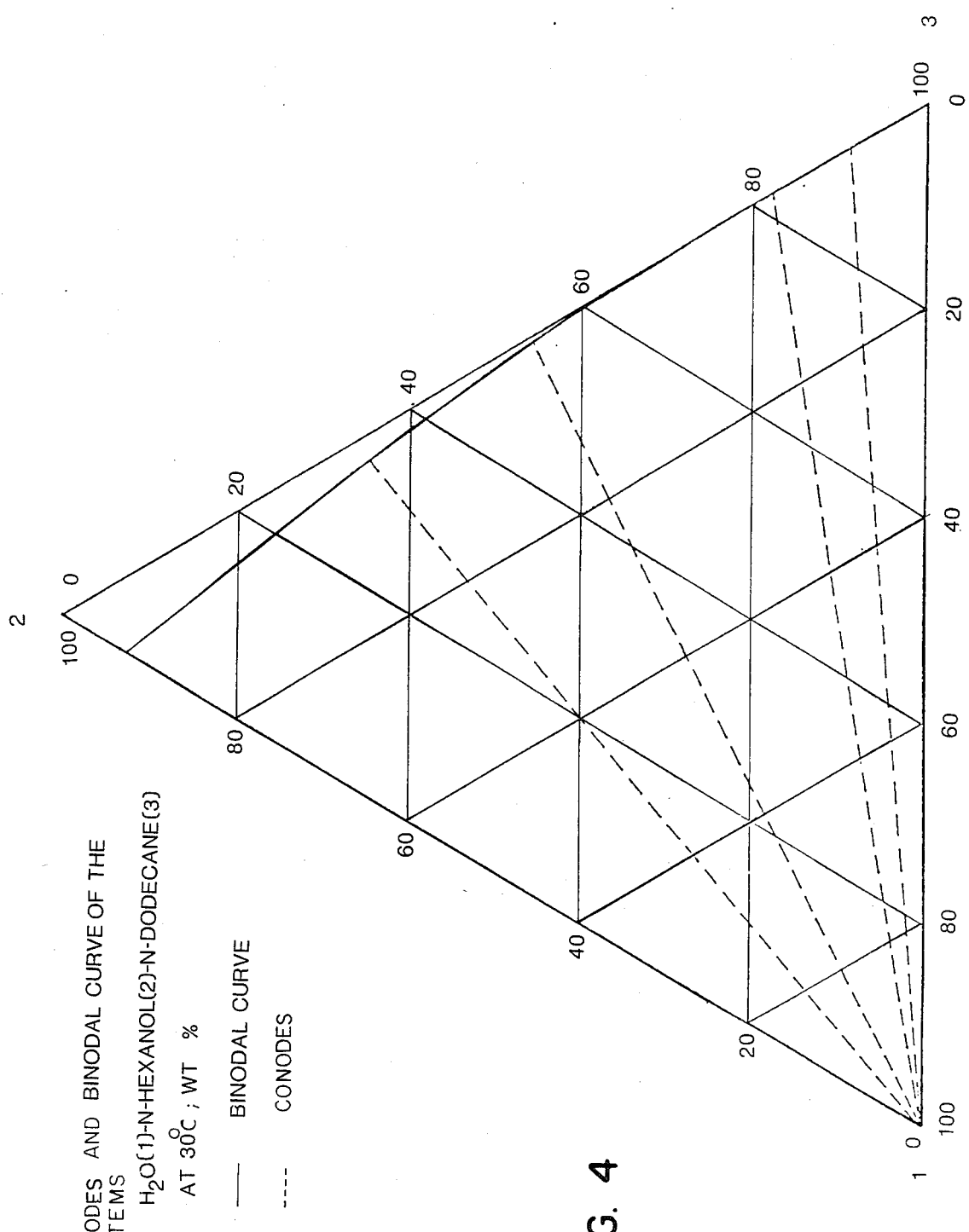

FIG. 4 is an example of corresponding behavior for n-dodecane as extraction solvent.

In another version of the invention-based method (FIG. 2), solvent I (SI) is separated from solvent II (SII) by distilling it from extract phase II (EII) which flows off in extraction II. However, such a separation through simple distillation is only possible if no azeotrope is formed. Thus, solvent II has to have a boiling point which differs considerably from that of solvent I. In order to keep the energy requirements for this recovery process as low as possible, solvent I should be obtained as top product (S) from the rectifying plant II. Thus, solvent II has to have a higher boiling point than solvent I.

The ethanol content of raffinate I (RI) and that of raffinate II (RII) are nearly identical because of the low polarity of solvent II (SII). Extract phase II (EII) contains only traces of ethanol. The ethanol concentration in extract phase I and the solvent I concentration in extract phase II depend on the phase ratio selected for the respective extraction steps. In order to reduce this amount of solvent I in raffinate II to a minimum, however, it is necessary not to go below a certain phase ratio for extraction II. The layout of the extraction plant greatly influences this.

Figure 5:
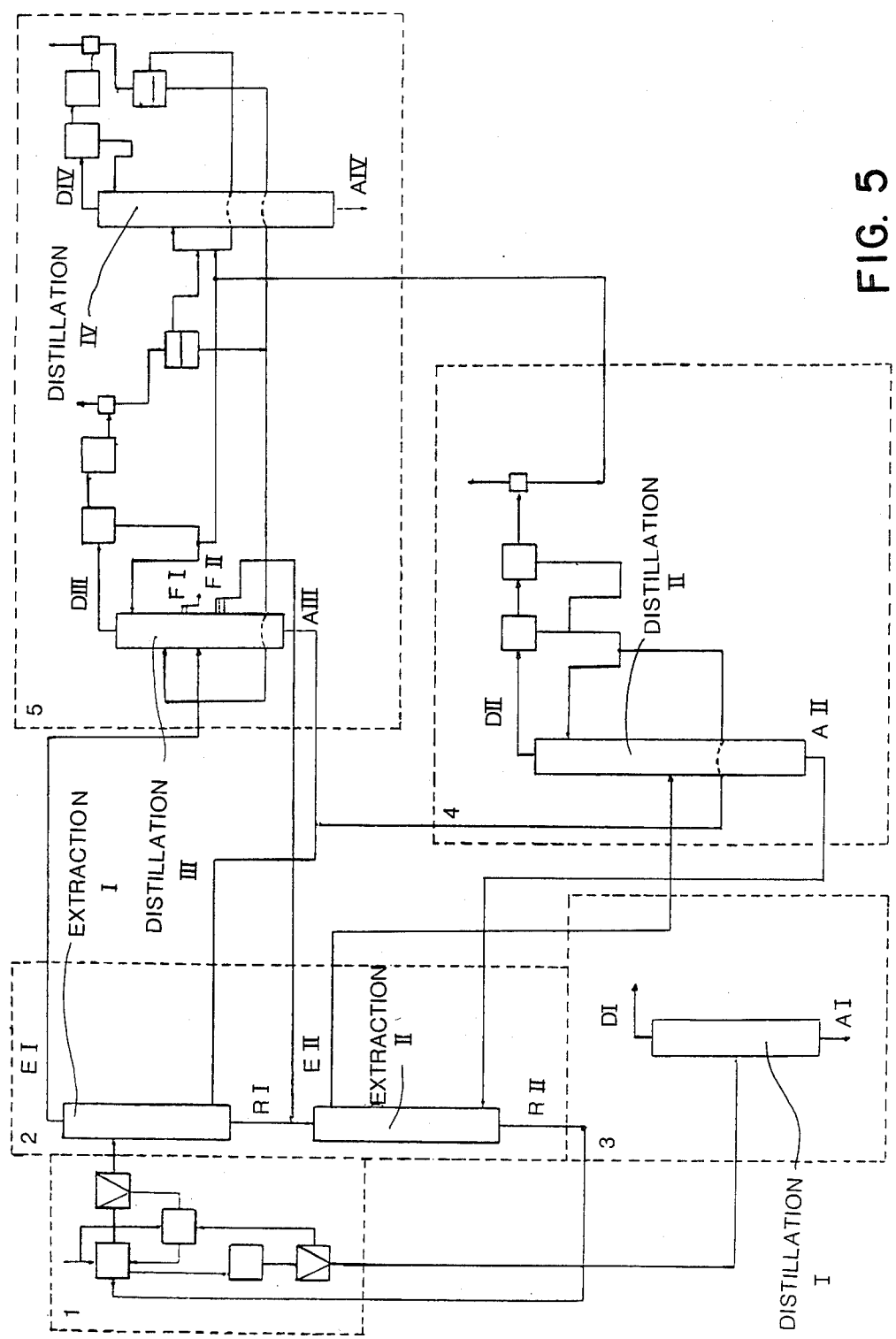
FIG. 5 is a flow diagram for the method which is integrated in a total process to produce polar organic compounds.

FIG. 5 shows another possible way of using this method within the framework of the total process. This version is divided into 5 partial processes.
1. fermentation
2. extraction
3. to 5. recovery processes through distillation.

Figure 2:
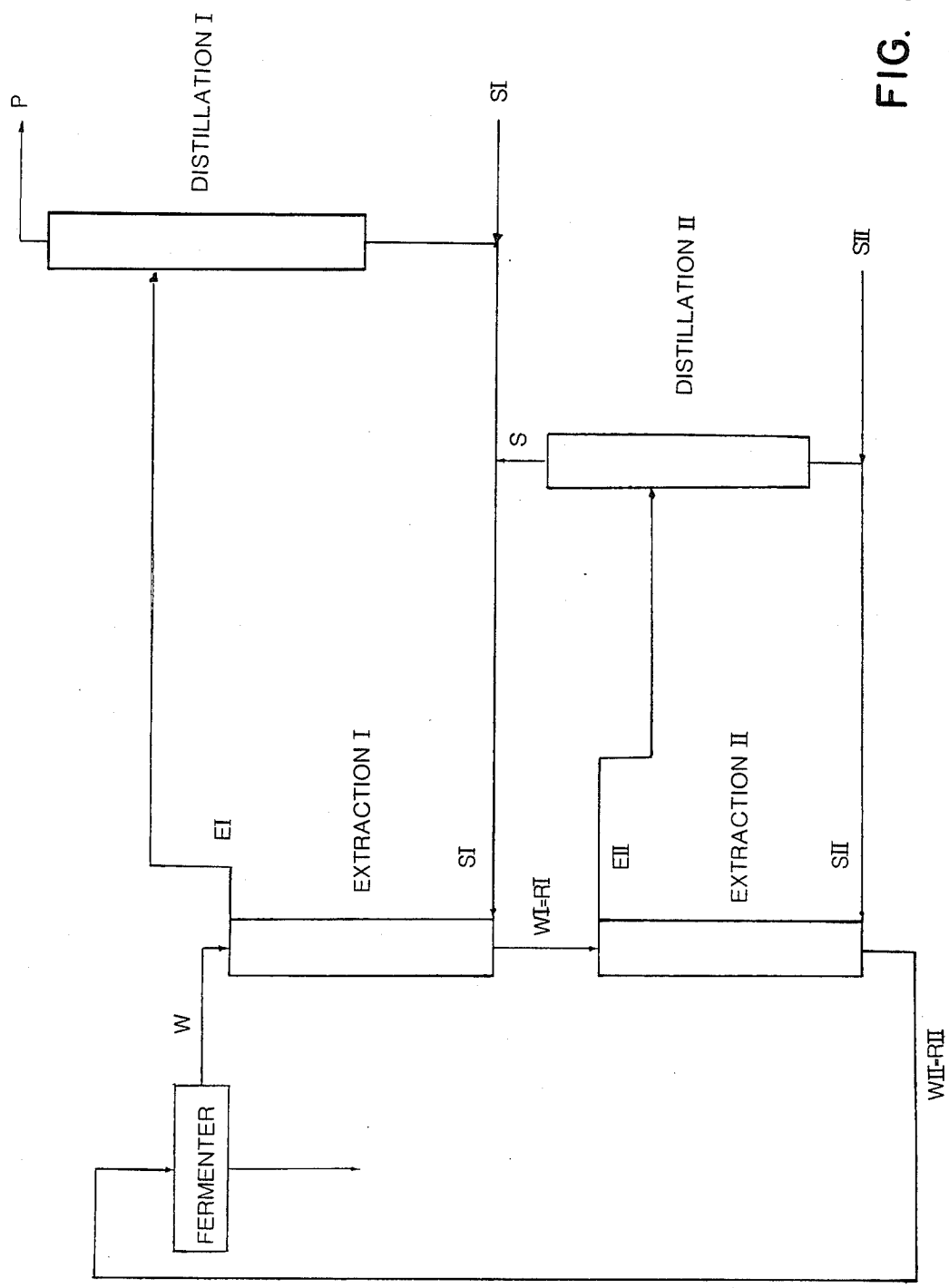
FIG. 2 is a flow diagram for that method, which is carried out by recovering extract phases I and II through distillation, FIGS. 3 & 4 reflect the fluid/fluid equilibrium behavior of the two solvent systems in use.

The sections 2, 4 and 5 are different variations of the method shown in FIG. 2.

Section 1 depicts continuous fermentation with yeast recovery and a flow which leaves this continuous process.

Section 3 shows separation through distillation of the polar organic compound DI from flow AI which leaves the process.

A II of section 4 denotes extraction solvent II and DII of solvent I.

In Section 5, flow A III, which flows off in distillation III, is equivalent to solvent I. A IV depicts the pure, polar organic compound obtained during azeotropic distillation; DIII is a head product of distillation III, which consists of water and the polar organic compound, and D IV is a ternary azeotrope, formed during distillation IV by using an entrainer, and which consists of $H_2O$, the polar organic compound and entrainer. FI and FII are side flows which are to be drawn off. The composition of the extract phase I (EI) is so advantageous that it allows in section 5 an energy-favorable thermal recovery of the above mentioned organic polar compounds, in particular low aliphatic alcohols. Heat-flow coupling of the individual sections 1 to 5 improves the total process with respect to thermal efficiency.

Figure 6:
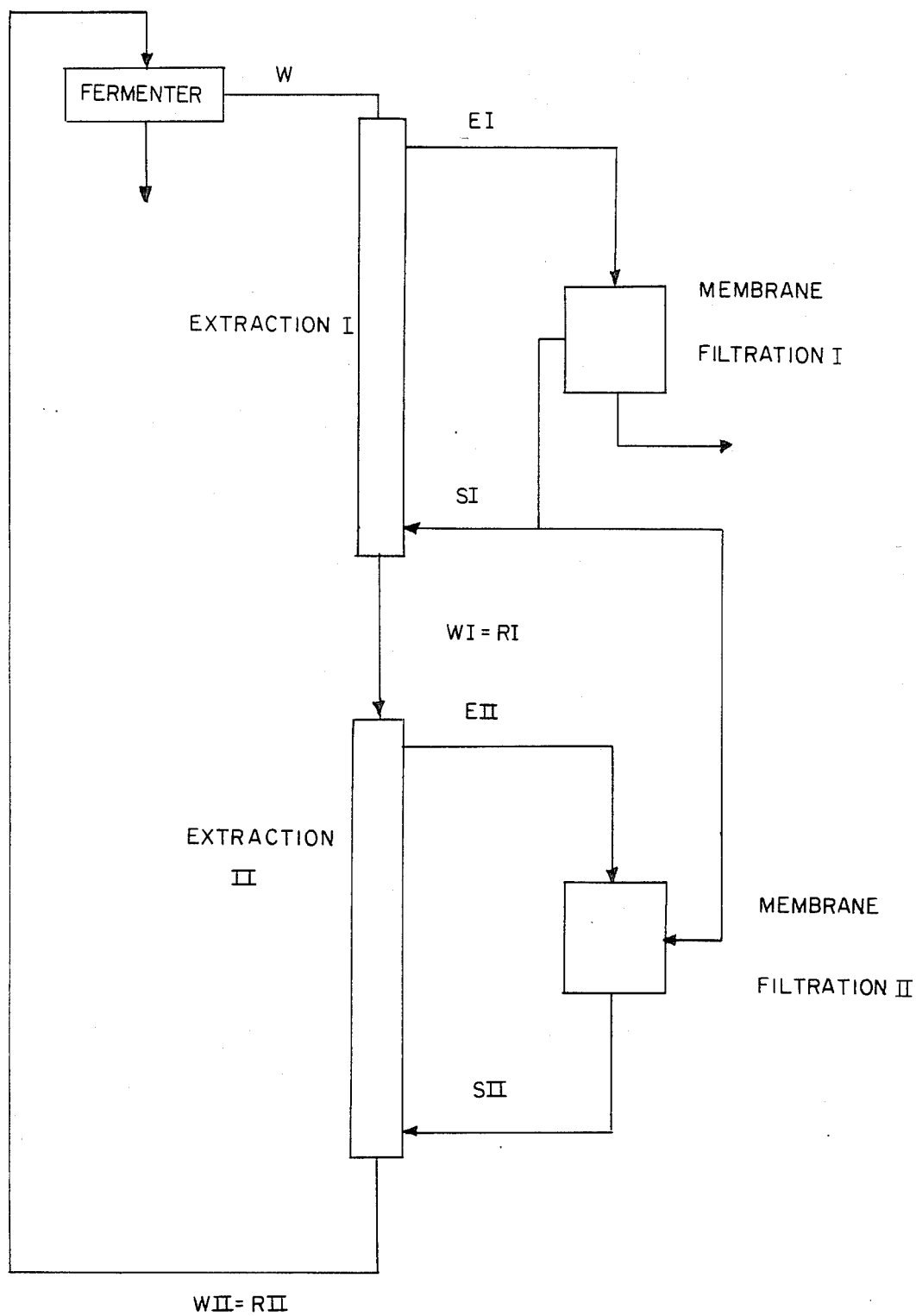
FIG. 6 is a flow diagram for that method which provides for a non-thermal recovery of extraction phases I and II.

FIG. 6 shows another version of the invention-based method. It is based on the use of a higher molecular solvent I (SI), which also has enough selectivity towards the polar, organic compound in the aqueous solution (W). Recovery, which follows extract phase I (EI) and extract phase II (EII), in this case consists of non-thermal procedural steps, which are based on a molecular weight difference as a criterion for separation (e.g., membrane filtration).

All method variations are based on the fact that, in order to improve the exchange of substances at the highest possible systems temperature for the extractors, extraction takes place at temperatures of up to 60° C.

EXAMPLE 1

As an example of how to use the method in accordance with the invention, we describe a continuous extraction, parallel to a continuous molasses fermentation, which takes place in a plant of the kind shown in FIG. 2.

From a fermenter, a molasses mash with 5% by weight ethanol was added to extraction I (W). An ethanol-free n-hexanol flow (approx. 3 to 4% by weight), which contained some residual water, was fed into the bottom of an extraction plant. This n-hexanol-$H_2O$-flow constituted the discharge of distillation plant I (SI). The residual water content was based on the formation of a binary azeotrope n-hexanol-water, which was purposely drawn off to lower the boiling temperature in the bottom of distillation plant I. The phase ratio (relating to mass) of the infeed phases to extraction I, W:SI, was 3:1. The ethanol concentration, as measured in extraction phase (EI) after an equilibrium had been reached for the total process, was 7.8% by weight. The outflowing aqueous phase (WI) of extraction I contained residual ethanol amounts of 2.4% by weight. This aqueous phase (WI) provided the inflow of aqueous phase for extraction II. The bottom product of distillation II consisted of 100% n-dodecane (SII), the extraction solvent II. This was fed into the bottom of extraction II as solvent flow. The phase ration WI:S, which had to be observed here, was also 3:1. Besides negligable traces of ethanol and water, which were removed at second cooler of distillation unit II, extract phase II (EII) also contained 5.4% by weight n-hexanol.

This n-hexanol portion was separated from solvent II (n-dodecane) in distillation II and added to the solvent flow (SI).

The raffinate II (RII) which did flow off in extraction II, contained 2.4% by weight ethanol and traces of both solvents n-hexanol and n-dodecane (their sum was smaller than 0.05% by weight). This loss of solvents in the invention-based method was made up by adding the lost amounts again at the right points (see FIG. 2). Because only about ⅓ of the aqueous phase was removed from the cycle process through separate recovery of part of the fermentation fluid, the corresponding solvent losses were extremely low. Further process parameters and test results can be seen from Table 1.

TABLE 1

| Extraction | Solvent | W/SI WI/SII | SI/SII W,WI (kg/h) | P (kg/h) | S (kg/h) | *1 $H_2O$ % Wt. | Phase Composition | | | Phase |
|---|---|---|---|---|---|---|---|---|---|---|
| | | | | | | | Ethanol % Wt. | n-Hexanol % Wt. | n-dodecane % Wt. | |
| I | n-hexanol | 3:1 | 1.5 W | .04 | — | 95 | 5 | — | — | W |
| | (SI) | | .5 SI | | | 6 | 7.8 | 86.2 | — | EI |
| | | | | | | 95.9 | 2.4 | 1.7 | — | RI |
| | | | | | | 3.6 | 0 | 96.2 | — | SI |
| II | n-dodecane | 3:1 | 1.45 WI | — | 0.026 | 95.9 | 2.4 | 1.7 | — | WI = RI |
| | (SII) | | .48 SII | | | 0.01 | 0.01 | 5.4 | <94.6 | EII |
| | | | | | | 97.5 | 2.4 | 0.02 | 0.02 | RII |
| | | | | | | — | — | — | 100 | SII |

*1 Extractions I and II were carried out with pulsating perforated bottom columns. Percentages by weight, which refer to the aqueous phase, do not take the dry substance content into account.

EXAMPLE 2

Another example for use of the invention-based method is a continuous extraction parallel to a continuous molasses fermentation in a plant, as shown in FIG. 6. Extract phase I, which is the result of extraction I, was here not separated into its constituent parts through distillation, but through a membrane filtration. A silicone oil of the type AK 10, produced by the company "Wacker-Chemie," was used as solvent I (SI). The separation limit for the membrane which was used, was molecular weight 500. The filtrate consisted of 80% by weight ethanol and 20% by weight water. Silicone oil could not be detected in it. The surplus was added to extraction I as solvent (SI). Minute amounts of the silicone oil in raffinate I were extracted from aqueous phase (SI) in extraction II with the aid of extraction solvent II(SII). The extraction solvent II was n-dodecane. The aqueous flow (WII), which flowed off in extraction II, was fed back into the fermentation. Extract phase II (EII), which contained the silicone oil, was also filtered through the membrane filter, whereby extraction solvent II (SII) in its pure form was recovered as filtrate and silicone oil (SI) as residual matter.

We claim:

1. Method for the separation of polar organic compounds from aqueous fermentation fluids which comprises:
   (a) extracting at least part of said fermentation fluid from a fermentation process with a first solvent (SI) which is a selective extractant for said polar organic compounds to form a first extract phase (EI) comprising first solvent (SI) and extracted polar organic compounds and a first raffinate phase (RI) comprising the remaining aqueous fermentation fluid and some solvent (SI);
   (b) separating said first extract phase (EI) from said first raffinate phase (RI);
   (c) recovering said polar organic compounds from the said first extract phase (EI);
   (d) extracting said first raffinate phase (RI) with a second solvent (SII) which is a selective solvent for the first solvent (SI) and which has a different polarity than solvent (SI) to form a second extract phase (EII) comprising first solvent (SI) and second solvent (SII), a second raffinate phase (RII) substaltially free from said solvent (SI), solvent (SII) and said polar organic compounds.
   (e) separating said second extract phase (EII) from said second raffinate phase (RII).

2. Method in accordance with claim 1, wherein said (SII) is substantially less polar than said solvent (SI).

3. Method in accordance with claim 1, wherein said fermentation fluid is extracted at temperature above 20° C.

4. Method in accordance with any one of claims 1 to 3 wherein in step (a), at least one n-alkanol with 4 or more carbon atoms is used for extracting.

5. Method in accordance with claim 4 wherein solvent (SII) has almost no selectivity for the polar organic compounds still contained in raffinate phase RI.

6. Method in accordance with claim 4 wherein solvent SII is a C5–C18 alkane.

7. Method in accordance with claim 4 wherein in step (c), said polar organic compounds are recovered by fractional distillation.

8. Method in accordance with claim 4 wherein solvents (SI) and SII) are recovered in a thermal separation step and are recycled to the steps (a) and (d) respectively.

9. Method in accordance with claim 4 wherein n-hexanol is used as first solvent (SI) and n-dodecane as second solvent (SII).

10. Method in accordance with claim 4 wherein in step (a), a solvent with molecular weight above 200 is used for extractionn and wherein extracts EI and EII each are separated from phases RI and RII without application of heat.

11. Method in accordance with claim 4 wherein extraction and recovery are preformed simultaneously with said fermentation.

12. Method in accordance with claim 4 wherein phase RII is recycled to said fermentation process.

* * * * *